United States Patent [19]
McCaffrey et al.

[11] Patent Number: 5,679,648
[45] Date of Patent: Oct. 21, 1997

[54] METHODS FOR THE TREATMENT AND PREVENTION OF FUNGAL INFECTIONS BY ADMINISTRATION OF 3'-DEOXYPURINE NUCLEOSIDES

[75] Inventors: Ronald P. McCaffrey, Needham; Alan M. Sugar, Wellesly, both of Mass.

[73] Assignee: The University Hospital, Boston, Mass.

[21] Appl. No.: 351,067

[22] Filed: Nov. 30, 1994

[51] Int. Cl.$^6$ .................................................. A61K 31/70
[52] U.S. Cl. ...................... 514/46; 514/45; 536/27.21; 536/27.6; 536/27.61; 536/27.62; 536/27.63; 536/27.7; 536/27.8; 536/27.81
[58] Field of Search ................... 514/46, 45; 536/27.6, 536/27.61, 27.62, 27.63, 27.7, 27.8, 27.81, 27.21

[56] References Cited

U.S. PATENT DOCUMENTS

| | | | |
|---|---|---|---|
| 4,163,839 | 8/1979 | Umezawa et al. | 536/27.13 |
| 4,432,348 | 2/1984 | Nakatsugawa | 128/1.1 |
| 4,434,788 | 3/1984 | Nakatsugawa | 128/1.1 |
| 4,594,320 | 6/1986 | Fujishima | 435/89 |
| 4,594,321 | 6/1986 | Fujishima et al. | 435/89 |
| 4,708,935 | 11/1987 | Suhadolnik et al. | 435/91 |
| 4,997,818 | 3/1991 | McCaffrey et al. | 514/45 |

FOREIGN PATENT DOCUMENTS

| | | |
|---|---|---|
| 1164346 | 3/1984 | Canada. |
| 0068268 | 6/1981 | European Pat. Off.. |
| 0376852 | 7/1990 | European Pat. Off.. |
| 4055596 | 5/1979 | Japan. |
| 5160795 | 12/1980 | Japan. |
| 1103831 | 5/1986 | Japan. |
| 3267723 | 11/1988 | Japan. |

OTHER PUBLICATIONS

Budavari et al. (eds), *The Merck Index*, 11th Ed., Merck & Co., Rahway, NJ, 1989, entry No. 2524 at p. 395.

Berkow et al. (eds), *The Merck Manual of Diagnosis and Therapy*, 16th Ed., Merck & Co., Rahway, NJ, 1992, see pp. 159–161, 266–267 and 2422–2423.

Jagger et al., "Inhibition of Ehrlich Mouse Ascites Tumor Growth by Cordycepin," *Cancer Research*, 21, 216–220 (1961).

Klenow, "Formation of the Mono–, Di–, and Triphosphate of Cordycepin in Ehrlich Ascites–Tumor Cells In Vitro", *Biochim. Biophys. Acta*, 76, 347–353 (1963).

Shigeura et al., "Utilization of 6–Methylamino–9–(3'–deoxy–β–D–ribofuranosyl) purine by KB Cells," *Biochim. Biophys. Acta*, 138, 26–34 (1967).

Wagner et al., "Effects of Purines and Pyrimidines on the Fungistatic Activity of 5–Fluorocytosine in Aspergillis Species", *Antimicrobial Agents and Chemotherapy*, 11(2), 229–233 (1977).

Hall et al., "Antiviral Drug and Interferon Combinations," Ch. 3 in *Antiviral Agents: The Development and Assessment of Antiviral Chemotherapy*, vol. II. H. J. Field (ed.), CRC Press, Boca Raton, FL, 1987, pp. 29–84, see especially pp. 41–43.

Parsons et al., "Human Melanoma Cells Sensitive to Deoxyadenosine and Deoxyinosine," *Biochemical Pharmacology*, 35(4), 655–660 (1986).

Parsons et al. (II), "selective Toxicity of Deoxyadenosine Analogues in Human Melanoma Cell Lines," *Biochemical Pharmacology*, 35(22), 4025–4029 (1986).

Kouni et al., "Metabolism of Adenosine Analogues by *Schistosoma mansori* and the Effects of Nucleoside Transport Inhibitors," *Biochemical Pharmacology*, 36(7), 1099–1106 (1987).

Queen et al., "In Vitro Susceptibilities of *Plasmodium falciparum* to Compounds Which Inhibit Nucleotide Metabolism," *Antimicrobial Agents abd Chemotherapy*, 34(7), 1393–1398 (1990).

Henderson et al., "On the Mechanism of Feedback Inhibition of Purine Biosynthesis de Novo in Ehrlich Ascites Tumor Cells in Vitro," *J. Biol. Chem.*, 240(7), 3104–3109 (1965).

McCaffrey, "Cordycepin Activates An Apoptotic Cascade in TdT–Positive Leukemia Cells," Abstract from the 35th Annual Mtg. Am. Soc. Hematology, Dec. 3–7, 1993.

Abstract—Johns, et al., "Enhancement of the Biological Activity of Cordycepin (3'Deoxyadenosine) by the Adenosine Deaminase Inhibitor 2'–Deoxycoformycin", Biochem. Pharmacol., vol. 25, No. 12, Oct. 11, 1976.

Abstract—Adamson, et al. "Enhancement of the Biological Activity of Adenosine Analogs by the Adenosine Deaminase Inhibitor 2'–Deoxycoformycin", Pharmocology, vol. 15, No. 1, May 9, 1977.

Abstract—Yamasa Shoyu KK "Cordycepin and (2')–deoxycoformicin prepd. simultaneously by culturing a strain of Aspergillus or Emericella" JP,A,52 130 991, Nov. 2, 1977.

(List continued on next page.)

*Primary Examiner*—John Kight
*Assistant Examiner*—L. Eric Crane
*Attorney, Agent, or Firm*—James Remenick; Baker & Botts, L.L.P.

[57] ABSTRACT

This invention relates to compositions comprising an adenosine derivative and a deaminase inhibitor for the prevention and treatment of fungal and fungal-like infections. Infections which are treatable and preventable with these compositions are responsible for fungal diseases such as candidiasis, cryptococcosis, blastomycosis, aspergillosis, paracoccidiodomycosis and coccidioidomycosis, and the fungal-like diseases nocardiosis and actinomycosis. The invention also relates to methods for utilizing these compositions in treatment regiments. Treatments may be either in vivo or in vitro. In vivo treatments involve administration of compositions of the invention to mammals suspected or at risk of being infected with a fungal or fungal-like organism. In vitro treatments involve incubation of cells, tissues, food products, biological products derived from living materials or foods with compositions of the invention.

57 Claims, 1 Drawing Sheet

OTHER PUBLICATIONS

Abstract—"Cordycepin Is Selectively Cytotoxic For TdT–Positive Cells," Yener Koc, The American Society of Hematology, 34th Annual Meeting, 1992.

Abstract—"Cordycepin Selectively Kills TdT–Positive Cells," Yener Koc, ASCO, 35th Annual Meeting, 1993, May 16–18.

Abstract—"Induction of Apoptosis In TdT Leukemia/Lymphoma Cells By Cordycepin (3'–dA)," Yener Koc, ASCO Annual Meeting, May 14–17, 1994.

"Adenosine Analogues As Antimetabolites Against *Plasmodium falciparum* Malaria," Coomber, et al., *International Journal for Parasitology*, vol. 24, No. 3, pp. 357–365, 1994.

"Adenosine Deaminase From Human Erythrocytes: Purification and Effects of Adenosine Analogs," Agarwal, et al., *Biochemical Pharmacology*, vol. 24, pp. 693–701, 1975.

"Antimalarial Action of Nitorbenzylthioinosine in Combination with Purine Nucleoside Antimetabolites," Gero, et al., *Molecular and Biochemical Parasitology*, vol. 34, pp. 87–98, 1989.

"Biochemistry of Plasmodium (Malarial Parasites)," Sherman, *Microbiological Reviews*, vol. 43, No. 4, pp. 453–495, Dec. 1979.

"Characterization of Adenosine Deaminase From the Malarial Parasite, *Plasmodium lophurae*, and Its Host Cell, The Duckling Erythrocyte", Schimandle, et al., *Biochemical Pharmacology*, pp. 115–122, 1983, vol. 32.

"Combination Therapy of Schistosomiasis by Tubercidin and Nitrobenzylthoinosine 5'–Monophosphate," Kouni, et al., *Proc. Natl. Acad. Sci. USA*, vol. 80, pp. 6667–6670, Nov. 1983.

"Enzymes of Purine and Pyrimidine metabolism From the Human Malaria Parasite, *Plasmodium falciparum*," Reyes, et al., *Molecular and Biochemical Parasitology*, vol. 5, pp. 275–290, 1982.

"Human Malaria Parasite Adenosine Deaminase, Characterization in Host Enzyme–Deficient Erythrocyte Culture," Daddona, et al., *The Journal of Biological Chemistry*, vol. 259, No. 3, pp. 1472–1475, Feb. 10, 1984.

"Incorporation of 2–Halogeno–2'–Deoxyadenosine 5–Triphosphates into DNA During Replication by Human Polymerases $\alpha$ and $\beta$," Hentosh, et al., *The Journal of Biological Chemistry*, vol. 265, No. 7, pp. 4033–4040, Mar. 5, 1990.

"Purine and Pyrimidine Metabolism in the Trypanosomatidae," Hammond, et al., *Molecular and Biochemical Parasitiology*, vol. 13, pp. 243–261, 1984.

"Purine Nucleoside Phosphorylase of the Malarial Parasite, *Plasmodium lophurae*," Schimandle, et al., *The Journal of Biological Chemistry*, vol. 260, No. 7, pp. 4455–4460, Apr. 10, 1985.

"Purines and Pyrimidines in Malarial Parasites," Gero, et al., *Blood Cells*, vol. 16, pp. 467–484, 1990.

"Purine Salvage and Metabolism in *Babesia bovis*," Matias, et al., *Parasitol Res.*, vol. 76, pp. 207–213, Feb. 1990.

"Pryimidine Analogues," Hochster, et al., Metabolic Inhibitors, *A Comprehensive Treatise*, vol. 1, pp. 239–285, 1963.

"Quantitative Assessment of Antimalarial Activity In Vitro by a Semiautomated Microdilution Technique," Desjardins, et al., *Antimicrobial Agents and Chemotherapy*, vol. 16, No. 6, pp. 710–718, Dec. 1979.

"Stage–Specific alteration of Nucleoside Membrane Permeability and Nitrobenzylthioinosine Insensitivity in *Plasmodium falciparum* Infected Erythrocytes," Gero, et al., *Molecular and Biochemical Parasitology*, vol. 27, pp. 159–170, Jan. 1988.

"Synchronization of *Plasmodium falciparum* Erythrocytic Stages in Culture," Lambros, et al., *J. Parasitol*, vol. 65, No. 3, pp. 418–420, 1979.

Kerr et al., "The Toxicity of Adenosine Analogues Against *Babesia bovis* In Vitro," *Journal for Parasitology*, vol. 21, No. 6, pp. 747–751, 1991.

Abstract—"Cordycepin Activates An Apoptotic Cascade in TdT–Positive Leukemia Cells," McCaffrey, The American Society of Hematology, 35th Annual Meeting, Dec. 3–7, 1993.

FIG. 1

METHODS FOR THE TREATMENT AND PREVENTION OF FUNGAL INFECTIONS BY ADMINISTRATION OF 3'-DEOXYPURINE NUCLEOSIDES

RIGHTS IN THE INVENTION

This invention was made with United States Government support under grant number CA 52020, awarded by the National Cancer Institute of the National Institutes of Health, and the United States Government has certain rights in the invention.

BACKGROUND OF THE INVENTION

1. Field of the Invention

This invention relates to compositions and methods for the prevention and treatment of infections caused by fungal and fungal-like organisms. Compositions contain an adenosine derivative and a deaminase inhibitor, and may be used in vivo to treat or prevent infectious diseases or in vitro to inactivate infectious organisms in cultured cells, in fluids such as blood and blood products, in biological product derived from cells suspected of being contaminated and in foods.

2. Description of the Background

Mycology is the study of fungi, commonly considered the yeasts and molds. Medical mycology concerns itself with those organisms which cause diseases in humans and other animals. Most of the clinically important mycotic organisms are eukaryotic, however, there is a unique group of bacteria that grow as branched, long or short filaments just like the fungi. These fungal-like prokaryotes are the actinomycetes and they comprise at least eight different families.

Most of the actinomycetes are harmless although a few are pathogenic to humans. The most notable of those are *Nocardia asteroides* and *N. brasiliensis*, the causative agents of nocardiosis, and *Actinomyces israelii*, the causative agent of actinomycosis. Nocardiosis occurs most frequently in the respiratory tract and manifests itself as a respiratory disorder. A typical disease course involves the development of one or more lung abscesses which enlarge over time forming cavities. Organisms spread from the lungs into the blood and establish themselves throughout the body forming abscesses. These abscesses destroy soft tissues and bone and can erupt through the skin. Once metastasis has occurred there is little chance for recovery. Treatments typically involve systemic administration of sulfadiazine, but the prognosis is always poor. Patients with nocardiosis are usually immunocompromised and will respond poorly to any treatment. Resistance to treatments also tends to be fairly common.

Another of the fungal-like bacteria is *Actinomyces israelii*. These organisms, unlike Nocardia exist as a part of the normal flora of most mammals including humans. Infections tend to initiate from an endogenous source. Cervicofacial actinomycosis occurs as a result of trauma to the mucous membranes of the head. Early symptoms include pain with an associated lumpy-swelling of mucous membranes of the jaw. As the swelling subsides, organisms spread throughout the body. Sites where infections take hold can extend through the skin forming abscesses. These organisms often infect the oral cavity in patients with poor dental hygiene.

Abdominal actinomycosis is typically caused by ingestion of organisms into a weak or debilitated gastrointestinal tract. Infections can perforate the intestine forming ulcerations which extend into the major organs such as the liver, urogenital system and bone. Penicillin and its derivatives are the treatment of choice, but chlortetracycline, chloramphenicol, streptomycin, sulfadiazine and other sulfonamides have been shown to be useful.

True fungi are eukaryotic organisms which grow as single cells or long-branched, filamentous structures. Most have both a sexual and an asexual stage. There are few major classes which cause diseases in humans although, to a large degree, their complete pathology is best described as unclear. Many produce enzymes and toxins which can be allergenic to a host, while others cause physical damage and destruction to tissues.

Fungal pathogens of humans can be divided into two categories. Those that infect superficially and those that invade and infect the deep organs and tissues. Four important families which are pathogenic in humans are the Zygomycetes, the Basidiomycetes, the Ascomycetes and the Deuteromycetes. The Zygomycetes all lack regular septa (cross-walls) in their hyphal filaments and cells typically possess multiple nucleic. Zygomycetes are a typical opportunistic and nosocomial infections (mucormycosis) caused by various species of breadmold fungi including the genera Mucor, Absidia, Rhizopus, Cunninghamella and other Mucorales. A few cause human disease which can become serious in the immunosuppressed and other immunocompromised individuals. As most patients with mucormycosis have a serious underlying disorder, effective treatment is often impossible.

Another large group of pathogenic fungi are Deuteromycetes which include a large number of organisms which typically colonize superficial lesions of the skin. Cutaneous infections tend to be restricted to keratinized tissues, but the Deuteromycetes can also cause deep-seated systemic infections that can become life-threatening.

Those organisms which typically infect superficially include *Trichophyton rubrum*, *T. mentagrophytes* and *T. floccosum*. These are the organisms most often responsible for tinea pedis, also referred to as athlete's foot. An estimated 30%–70% of the population of the Western world is believed to be at least subclinically infected. Chronically infected patients can develop hypersensitivity and a severe allergic response. Most have to deal with milder symptoms which include itchy peeling skin and ulcerations and cracking of the dermis.

Ringworm, tinea corporis, may occur anywhere on the body and is not restricted to humans. Various species of dermatophytes cause ringworm including *T. mentagrophytes* and *T. rubrum*, both of which can be spread from animals to humans. Most infections of normal healthy individuals will clear with time. Ringworm of the nail, tinea unguium (onychomycosis), is a common infection of toe nails. Although most infections are minor, tinea unguium is always associated with systemic dermatophyte infections.

Tinea capitis is a common skin infection that appears as red scaly lesions on the body with associated hair loss (alopecia) of the infected area. The most common etiological agents are *T. tonsurans, Microsporum audouini* and *M. canis*. Inflammatory reactions can produce deep ulcers with permanent alopecia.

Treatments for these diseases are all fairly similar and involve topical applications of long-chain fatty acids, salicylic acid, selenium sulfide and sulfur in ointments. One current treatment is topical griseofulvin, an antibiotic produced by a penicillium-type mold. Treatments usually require weeks or months and in certain cases even years.

Deep tissue fungal infections are all very serious. In many cases, such a diagnosis is a death sentence. Most human disease associated with fungal and fungal-like infections are attributed to the Saccharomycetes and other members of the family Ascomycetes. These organisms reproduce as single- or multi-celled conidia, which are formed in conidiophores.

Species of the genera Candida are the most frequent causes of human fungal diseases. All appear as non-branching, boxcar-like chains of tubular cells called pseudohyphae that bud, forming blastospores. These organisms colonize the oral cavity, gastrointestinal tract and vagina of many otherwise healthy individuals. These fungi can become pathogenic with a change in, for example, the pH or chemical make-up of their immediate local environment, or by antibiotic suppression of the surrounding organisms. Some of the species commonly associated with disease include *Candida krusei, C. glabrata, C. parapsilosis* and *C. tropicalis*. The most common species responsible for disease in humans is *Candida albicans*.

The most common forms of candidiasis are associated with mucosal, oral and vaginal infections. However, severe burns and surface wounds in patients with diabetes mellitus are frequently infected with *C. albicans*. Candidiasis of the oral cavity is referred to as thrush. It is common in bottle-fed newborns and as a complication of gum diseases. Vaginal candidiasis is common in many healthy women taking oral contraceptives or antibiotics, or during pregnancy. Cutaneous eczematoid candidiasis can arise in any area of the skin which remains warm and moist for long periods of time. All cases tend to respond well to drug therapy such as administration of wide-spectrum anti-fungal drugs. Cutaneous infections also respond readily to treatment of the underlying condition. Chronic infections with no obvious associated cause are more difficult to treat and may persist because of an underlying defect in T cell-mediated immunity or the presence of a polyendocrine deficiency in the patient such as hypoparathyroidism, hypoadrenalism or hypothyroidism.

In most cases, severe invasive candidiasis with visceral dissemination is indicative of a serious underlying disorder associated with immunosuppression or neutrophil depletion. Invasive candidiasis of the deep tissues can initiate from deep incisions or direct inoculation into the blood. Sources include intravenous lines, catheters, intravenous drug abuse, and all forms of surgical procedures. Infections are common in the immunocompromised and immunosuppressed who can easily become septic. Although not usually as rapidly progressive as bacterial sepsis, candidal sepsis has similar clinical manifestations including disseminated intravascular coagulation (DIC), shock, renal failure, lung and liver complications, and associated cardiac problems. Renal involvement is seen in over 90% of invasive cases. Prognosis is often poor.

Pathogenic fungal and fungal-like organisms tend to establish themselves, as would be expected, in the sinuses, orbit and brain, giving rise to, for example, rhinocerebral mucormycosis. In the lungs, candida lesions are often extensive and hemorrhagic. Meningitis, intracerebral abscesses, enteritis, arthritis and osteomyelitis are some common presentations of fungal and fungal-like diseases. Nevertheless, in certain cases, infections may cause no inflammatory reaction or a suppurative response.

Although a number of specific stains and culturing conditions have been developed, a definitive diagnosis of candidiasis is often difficult to make and to confirm, as the organisms are nearly ubiquitous over the entire body. Presence anywhere within the body cavity however is always definitive evidence of infection.

*Aspergillus fumigatus, A. niger* and other species of Aspergillus rank very closely behind Candida as common causes of fungal infections. Certain species can damage an otherwise healthy individual by mere inhalation of spores. Such individuals are hypersensitive to the spores and manifest an extreme inflammatory reaction. Other species produce damaging toxins. *A. flavus,* although not commonly infectious to humans, produces a liver carcinogen frequently found in many edible foods such as vegetables, fruits, breads, dairy products and even meats.

A diagnosis of colonizing aspergillosis implies growth of fungus in the pulmonary tract with minimal tissue invasion. Proliferating masses of fungal hyphae called fungus balls can be seen as brownish masses in pulmonary cavities. Invasive aspergillosis is an opportunistic infection typically found only in immunocompromised and debilitated hosts. Lesions occur primarily in the lungs, but also in the brain, kidneys and heart valves. Pulmonary lesions appear as necrotizing pneumonia with sharply delineated, rounded gray foci. These infections are rapidly progressive and life-threatening.

Another of the deep-tissue fungal infections is cryptococcosis, typically caused by *Cryptococcus neoformans*. These organisms can cause infections in healthy individuals exposed to massive numbers of spores, but most infections are restricted to immunocompromised patients. Patients with Hodgkin's disease and other leukemias and lymphomas may have associated cryptococcus infections. Pulmonary cryptococcus can be distinguished from other lung infections by definitive identification of the fungus in sputum or at biopsy using the latex cryptococcal antigen test (LCAT).

Blastomycosis, typically an infection of *Blastomycetes dermatitis,* is a chronic infection that can be characterized by focal suppurative and granulomatous lesions most commonly in the lungs and skin. Any area of the body can be affected including the internal organs. Symptoms can resemble tuberculosis or other mycoses and even malignant ulcers. Minor infections can resolve in healthy individuals, but late stage diseases require antifungal therapy.

Paracoccidiodomycosis, or South American blastomycosis is caused by *Paracoccidioides brasiliensis.* It is endemic in certain areas from Mexico to Argentina. The disease usually presents itself as extra-pulmonary lesions of the mouth, nose and larynx that spreads to local lymph nodes. All organs and organ systems are susceptible. Again, most short term treatments are unsuccessful. Therapy for years often can control the disease.

Coccidioidomycosis, another fungal disease, is caused by the inhalation of spores of the organism, *Coccidioides immitis*. These organisms cause an acute and chronic infection, similar to tuberculosis and primarily in the lungs. Approximately 60% of infected patients are asymptomatic. Another 10% present symptoms of mild coughing or fever (San Joaquin valley fever). Only about 0.2% of infected patients have more severe symptoms such as chilis, fever, weight loss and a general wasting. Central nervous system involvement and bone destruction can occur in the very serious cases. Such individuals are believed to have an unidentified cell-mediated immune deficiency.

Infections caused by Histoplasma capsulatum are endemic and rival the frequency of tuberculosis in the United States. This organism can be acquired by the inhalation of infected dust contaminated with bird or bat droppings. As with most fungal infections, pulmonary involvement is most common which can be asymptomatic or spread to any organ or tissue when unchecked by a healthy immune system.

The treatment of choice for almost all forms of fungal infections is amphotericin B. It can only be given intravenously and in many cases, amphotericin B is the only treatment available. Unfortunately, many organisms are not sensitive to its effects. Oral azoles such as mycoconazole, ketoconazol, fluconazole and itraconazole, which are less toxic than amphotericin B and can be administered orally, are increasingly being used to treat certain of the mycoses.

SUMMARY OF THE INVENTION

The present invention overcomes the problems and disadvantages associated with current strategies and designs and provides new methods for the treatment and prevention of diseases and disorders related to infection by fungal and fungal-like organisms.

One embodiment of the invention is directed to compositions containing an adenosine derivative and, optionally, a deaminase inhibitor. Examples of useful adenosine derivatives include cordycepins, cordycepin analogs and derivatives, and modifications of these molecular structures. Examples of useful deaminase inhibitors include coformycins, coformycin analogs and derivatives and modifications thereof. Preferably, the adenosine derivative is in an excess over the deaminase inhibitor. These compositions can be used in vivo for the treatment or prevention of fungal and fungal-like diseases in mammals or in vitro for the treatment of biological products suspected of being contaminated with an infectious organism.

Another embodiment of the invention is directed to methods for the treatment of patients suspected of being infected with fungal and fungal-like organisms comprising the administration to the patient of an adenosine derivative and, optionally, a deaminase inhibitor. Treatments may be administered parenterally, sublingually, enterally, by pulmonary absorption or by topical application. Adenosine may be administered simultaneously with or shortly before or after the deaminase inhibitor. Patients which may be successfully treated include most mammals such as humans. These methods can result in complete elimination of infectious organisms from the patient and resolution of all symptoms associated with infection.

Another embodiment of the invention is directed to methods for the prevention of infection by fungal and fungal-like organisms. A patient at risk of being infected is administered an adenosine derivative and, optionally, a deaminase inhibitor.

Another embodiment of the invention is directed to methods for the treatment of a biological product such as living cells or tissues suspected of or at risk of being infected with a fungal or fungal-like organism to prevent or eliminate the contamination. Treatments can be applied to, for example, whole blood, fractionated blood, plasma, serum, and transplantable organs, and most typically involves administration of an adenosine derivative and, optionally, a deaminase inhibitor.

Another embodiment of the invention is directed to methods for the treatment of a biological product such as material derived from living cells or tissues suspected of being contaminated with a fungal or fungal-like organism, or foods to prevent or eliminate the contamination. Treatments can be applied to products purified from cells such as cytokines, immune system regulators, recombinant proteins and blood products. Treatments involve administration of an adenosine derivative and, optionally, a deaminase inhibitor.

Another embodiment of the invention is directed to compositions and methods for the treatment and prevention of neoplastic disorders in patients. Patients, preferably humans, are administered compositions of the invention which comprise an adenosine derivative and, optionally, a deaminase inhibitor as described herein. Neoplastic disorders which can be treated include leukemias, lymphomas, sarcomas, carcinomas, neural cell tumors, squamous cell carcinomas, germ cell tumors, undifferentiated tumors, seminomas, melanomas, neuroblastomas, mixed cell tumors metastatic neoplasias, neoplasias due to pathogenic infections and other malignancies.

Other embodiments and advantages of the invention are set forth, in part, in the description which follows and, also in part, will be obvious from this description or may be learned from the practice of the invention.

DESCRIPTION OF THE INVENTION

As embodied and broadly described herein, the present invention is directed to compositions and methods for the treatment and prevention of fungal and fungal-like infections.

One embodiment of the invention is directed to pharmaceutical composition useful for the prevention and treatment of fungal and fungal-like infections in mammals. Compositions contain an adenosine derivative comprising a five-membered pentose ring coupled to a purine. Preferably, the adenosine derivative has the formula:

wherein $R_1$, $R_2$ and $R_3$ are each a chemical moiety such as hydrogen, hydroxyl, halide, alkyl or alkoxyl, amine or amide, sulfhydral, nitryl, phosphoryl, sulfinyl or sulfonyl, or a combination or derivative of these chemical moieties. Additionally, $R_1$, $R_2$ and $R_3$ and may be the same or different. More preferably, $R_1$ is OH, SH, $SCH_3$ or $NHCH_3$; $R_2$ is H, F, Cl, Br, I or $NH_2$; and $R_3$ is H, F, Cl, Br, I or $CH_3$. Examples of useful adenosine derivatives include cordycepin (3'-deoxyadenosine) and cordycepin derivatives. Derivatives may be identified from existing compounds by testing as herein described or as known in the art. Derivatives may also be organically or enzymatically created with techniques such as, for example, rational drag design and empirical screening using the disclosures provided herein and the knowledge of one of ordinary skill in the art.

Compositions of the invention are effective against a wide variety of fungal and fungal-like organisms. Examples of infections which can be treated by compositions of the invention include the fundal diseases candidiasis, tinea pedis, tinea corporis and tinea capitis, aspergillosis, mucormycosis, phaeohyphomycosis, cryptococcosis, coccidioidomycosis, blastomycosis, histomycosis, paracoccidiodomycosis and the Dematiaceous infections, and the fungal-like diseases nocardiosis and actinomycosis.

Treatable infections can occur in blood, tissues, the lymphatic system, the respiratory and gastrointestinal tract, the major organs and organ systems, and the dermis. Fungal organisms which are sensitive to treatments include *Candida krusei, C. glabrata, C. albicans* and *C. tropicalis,* the causative agents of candidiasis, and *Trichophyton rubrum, T. mentagrophytes, T. tonsurans, Microsporum audouini, M. canis* and *T. floccosum,* the causative agents of tinea pedis, tinea corporis and tinea capitis. Compositions can also be used to treat infections by *Nocardia asteroides* and *N. brasiliensis, Actinomyces israelii,* species of the genera Mucor, Absidia, Rhizopus, Cunninghamella and unrelated Mucorales, *Aspergillus fumigatus, A. flavus, A. niger* and other species of Aspergillus, *Cryptococcus neoformans, Paracoccidioides brasiliensis, Coccidioides immitis, Blastomycetes dermatitis* and *Histoplasma capsulatum.*

The mechanism of action of an adenosine derivative of the invention is directed to the disruption of enzymatic processes of the organism that relate to the metabolism of purine, purine derivatives and purine-like chemical structures. These processes are basic reactions that exist in all organisms. Purines and related compounds are involved, either directly or indirectly, in biosynthetic and enzymatic pathways such as nucleotide biosynthesis including the synthesis of ATP and GTP, nucleic acid and protein biosynthesis, intracellular and extracellular cellular signaling, mitosis, meiosis, DNA replication, RNA transcription, folate metabolism, the activities of protein kinase A and C, the purine cycle, excretion, absorption and secretion, and other processes considered fundamental to life. Fungal organisms are acutely sensitive to interference of these processes, and thus, compositions that specifically target these reactions can be used to selectively eliminate an infection or ameliorate the pathogenic symptoms associated with an infection without unnecessarily injuring the patient.

Compositions of the invention contain an adenosine derivative at a concentration of between about 1.0 nM to about 10 mM. Such compositions may be concentrated forms of the active ingredients or may be unconcentrated and suitable for immediate use. Alternatively, compositions which are liquids (vol./vol.) or solids (wt./wt.), may contain active components at between about 0.001% to about 100%, preferably between about 0.01% to about 10.0%, and more preferably between about 0.1% to about 5.0%, but may be further diluted, if necessary, such as for prolonged direct contact with skin or other bodily tissues where contact with more concentrated forms would be harmful. Compositions may also contain a pharmaceutically acceptable carrier to facilitate administration or introduction to a patient or biological product, to maintain or increase physiological stability, or to facilitate storage or half-life of the composition. Useful pharmaceutically acceptable carriers include water, various oils, salts, saccharides and polysaccharides, glycerols, collagens and combinations and modifications of these substances. Compositions of the invention may optionally include flavoring agents to increase palatability, and other agents that may be necessary or desirable to increase shelf-life, such as preservatives, anti-oxidants and other components advantageous for manufacture and distribution of the composition.

Compositions of the invention may optionally contain a deaminase inhibitor such as the adenosine deaminase inhibitor coformycin and derivatives of coformycin such as deoxycoformycin. Certain adenosine derivatives are enzymatically deaminated into inactive inosine by deaminases which may be present in the patient or the article to be treated. The addition of such an inhibitor prevents deamination of the adenosine derivative, and thus, its inactivation. Further, deaminase inhibitors can have an effective role in treatment. For example, deaminase inhibitors diminish the metabolism of deoxyadenosine to deoxyadenosine triphosphate and alter the activity of certain kinases and polymerases. These activities may also have a useful effect against the infecting organism. Deaminase inhibitors such as coformycin and deoxycoformycin are safe and non-cytotoxic at useful concentrations. Compositions of the invention which include a deaminase inhibitor contain this component at a concentration of between about 0.1 nM to about 1.0 mM. Alternatively, compositions which are liquids (vol./vol.) or solids (wt./wt.) may contain between about 0.001% to about 100%, preferably between about 0.01% to about 10.0%, and more preferably between about 0.1% to about 5.0% of the deaminase inhibitor, but may be, if necessary, further diluted.

Compositions of the invention containing both an adenosine derivative and a deaminase inhibitor will preferably have an excess of the adenosine derivative over the inhibitor. The adenosine derivative will preferably be in a two- to twenty-fold excess over the deaminase inhibitor and more preferably in a five- to ten-fold excess. The deaminase inhibitor may be administered prior to, subsequent to, or simultaneous with the adenosine derivative. The composition may contain these two ingredients in a mixture to be administered together or the two may be kept separate and administered separately. As both adenosine derivatives and deaminase inhibitors can be effectively dissolved in aqueous solutions, they can be easily utilized as mixtures in liquid or solid form.

Another embodiment of the invention is directed to compositions wherein the adenosine derivative is coupled to the deaminase inhibitor. Coupling may be by ionic bonding such as hydrogen bonding, covalent bonding and affinity bonding. Preferably, the bond formed is stable when used in vivo or in vitro. In compositions where the adenosine derivative and the deaminase inhibitor are separate, it may be difficult to effectively administer both components. Compositions wherein the two components are coupled together are effective for treating or preventing an infection because the deaminase inhibitor is effective in all locations where the adenosine derivative is active. Compositions can be used in vivo to treat human patients infected or suspected of being infected with a fungal or fungal-like organism, or in vitro to treat a biological product suspected of being contaminated with a fungal or fungal-like organism.

Another embodiment of the invention is directed to a method for treating a patient suspected of or at risk of being infected with a fungal or fungal-like organism. Diseases which can be treated include mycotic or mycotic-like infections of the blood, lymph and tissues such as candidiasis, aspergillosis, mucormycosis, blastomycosis, cryptococcosis, blastomycosis, histoplasmosis, coccidioidomycosis and paracoccidiodo-mycosis, nocardiosis and actinomycosis.

The patient being treated is administered a therapeutically effective amount of a composition of the invention. Patients which can be treated include mammals such as a dog, cat, horse, cattle, pig, rodents, or chicken, or a wild animal, but is preferably a human. Zoo animals, such as penguins and monkeys, are typically infected with a range of different fungal organisms and require treatment. As most fungal organisms can infect across species and genera boundaries, elimination of the fungal organisms in the animal is sometimes an effective means for eliminating or preventing infections in humans. As compositions of the invention are safe and non-toxic at effective concentrations, compositions can safely be used to treat both human and non-human infections.

Administration may be to an adult, an adolescent, a child, a neonate or an infant, or even to a patient in utero. Dosages range from about 1 ng/kg patient weight to about 10 mg/kg patient weight. Administration of the composition may be for a short term, continuous or sporadic as necessary. Patients with a suspected or diagnosed infections may only require treatments for short periods of time or until the infection has proceeded to remission or has been effectively eliminated. Alternatively, to effectively eliminate certain organisms, administration may require long term treatments such as for months or years. As compositions of the invention are generally safe and non-toxic at required dosages, this does not present a problem.

Compositions are administered in a manner which is most useful for the infection being treated. Useful methods of administration include oral, parenteral, sublingual, rectal or enteral administration, pulmonary absorption or topical application. Parenteral administration may be by intravenous injection, subcutaneous injection, intramuscular injection, intra-arterial injection, intrathecal injection, intraperitoneal injection or direct injection or other administration directly to the site or sites of infection. Injectable forms of administration are sometimes preferred for maximal systemic effect against systemic infections and infections of the respiratory tract and the deep tissues. When long term administration by injection is necessary medi-ports, in-dwelling catheters, or automatic pumping mechanisms may be used. These devices provide direct and immediate access to the arteries in and around the heart, the lungs and other major organs and organ systems. Such devices are useful for treating diseases that infect organs and organ systems.

Another effective method of administering compositions of the invention to infectious sites may be by transdermal transfusion such as with a transdermal patch, and other means of direct contact with affected tissues, or by administration to internal infection through an incision or some other natural or artificial opening into the body. Compositions may also be administered to the nasal passages as a spray. Diseases localized to the respiratory tract, the head and brain area are treatable in this fashion as arteries of the nasal area provide a rapid and efficient access to the upper areas of the body. Nasal sprays also provide immediate access to the pulmonary system and the bloodstream which may be the preferred method of administration against forms of infection. Access to the gastrointestinal tract is also achievable using oral, enema, or injectable forms of administration. Compositions may be administered as a bolus injection or spray, or administered sequentially over time (episodically) such as every two, four, six or eight hours, every day (QD) or every other day (QOD), or over longer periods of time such as weeks to months for as long as it takes the infection to resolve or for the patient's own system to be able to overcome the infection.

Orally active compositions are preferred as oral administration is usually the safest, most convenient and economical mode of drug delivery. Oral administration may often be the most effective method to administer compositions directed to parasites of the gastrointestinal tract. Oral administration can be disadvantageous because compositions are poorly absorbed through the gastrointestinal lining. Compounds which are poorly absorbed tend to be highly polar. Consequently, compounds which are effective, as described herein, may be made orally bioavailable by reducing or eliminating their polarity without significantly modifying their functional activity. This can often be accomplished by formulating a composition with a complimentary reagent which neutralizes its polarity, or modifying the compound with a neutralizing chemical group. Oral bioavailability is also a problem because drugs are exposed to the extremes of gastric pH and gastric enzymes. These problems can be overcome by modifying the molecular structure to be able to withstand the very low pH conditions and resist the enzymes of the gastric mucosa such as by neutralizing an ionic group, by covalently bonding an ionic interaction, or by stabilizing or removing a disulfide bond or other relatively labile bond.

When the composition is administered orally, it may be in the form of a liquid, a spray, a powder, a pill, a tablet or a capsule. To facilitate oral administration, compositions of the invention will preferably include flavoring agents and in all cases may contain other agents to increase shelf-life or as may be required or desired for ease of transportation and effective delivery.

Administration by any method can be accurately quantitated by measuring levels of the composition from a sample of bodily fluid such as blood, serum or plasma. Effective serum levels of active components of the invention such as the adenosine derivative or deaminase inhibitor are between about 0.01 nM to about 1.0 mM, preferably between about 1.0 nM to about 0.1 mM, and more preferably between about 10.0 nM to about 50.0 nM. Effective levels of the deaminase inhibitor may be between two- and twenty-times lower than effective levels of the adenosine derivative. When applied by direct contact, effective levels of active ingredient may sometimes be analyzed by determining concentration of the composition in the areas which are in close contact with the area of application. For example, when applied topically to the skin, effective levels may be determined from fluid or tissue samples of the dermal tissues within a few centimeters under the area of application. In such cases, composition strength may be predetermined and used as a concentrated solution.

Compositions can be administered by oral or enema formulations, or by rectal irrigation to maximize their contact with and effectiveness on the gastrointestinal system. In such cases, dosages are between about 1% to about 20% (vol./vol.) or between about 1 mM to about 100 mM. Doses are administered until symptoms improve sufficiently for the patient's immune system to resolve the infection or the parasite is killed or eliminated. Multiple and frequent dosing is not problematic because the compounds of the invention are safe, non-toxic and physiologically stable.

Positive effects of treatment include a reduction of organism load, death or inactivation of the organisms, decreased infectivity or spore-forming ability of the organism, or complete or nearly complete elimination of the infecting organism from the body. Preferably, the patient has an infection, as measured by any appropriate testing parameter, which is reduced at least 100-fold, more preferably 1000-fold, and even more preferably is undetectable after treatment. The presence of infection may be determined by growing organisms from biological samples obtained from the patient suspected to be infected into suitable cultures and counting the colonies which can be grown. Alternatively, biological samples are obtained from selected areas of the patient suspected to be infected and the numbers of organisms visualized directly or indirectly under a microscope or other suitable devise and counted. Fluorescent-conjugated antibodies may also be used in, for example, an ELISA or other markers to detect mycotic or related antigen or antiantigen antibodies in a biological sample to determine the degree of infection and the effect of treatments.

Another embodiment of the invention is directed to compositions of the invention which can be used in combination with other agents to maximize the effect of the compositions in an additive or synergistic manner. Agents which may be effective in combination with the compositions of the invention include other drugs and treatments which are known or suspected to have a positive effect against the fungal organism. Examples of additional agents known to be effective against one or more pathogenic fungal and fungal-like organisms include flucytosine, mycoconazole, fluconazole, itraconazole, ketoconazole and griseofulvin, antibiotics such as amphotericin B, sulfadiazine, penicillin, chlortetracycline, chloramphenicol, streptomycin and other sulfonamides, and derivatives, modifications and combinations of these agents. Therapies using various combinations of these agents would be safe and effective therapies against infections. Combinations of therapies may also be effective in inducing suppression or elimination of an infection such as compositions of the invention plus radiation therapy, toxin or drug conjugated antibody therapy using monoclonal or polyclonal antibodies directed against, for example, the organism, infected cells, gene therapy or specific anti-sense therapy. Effects may be additive, logarithmic, or synergistic, and methods involving combinations of therapies may be simultaneous protocols, intermittent protocols or protocols which are empirically determined.

Another embodiment of the invention is directed to compositions described above which can be used prophylactically. For example, patients exposed to areas where a fungal or fungal-like disease is endemic may be continuously treated with compositions to prevent an infection from taking hold. Patients who have been genetically screened and determined to be at high risk for the future development of an infection may also be administered compositions, possibly beginning at birth and possibly for life. Administration may be by any means described and dosages may be reduced in comparison to dosages required for treatment. Both prophylactic and therapeutic uses are readily acceptable because these compounds are generally safe and non-toxic at useful dosages.

Another embodiment of the invention is directed to methods for the treatment of biological products suspected of being contaminated with a fungus or fungal-like organism. Products which can be treated or pre-treated include, for example, whole blood, fractionated blood, plasma, serum, transplantable organs, living cells including bone marrow, stem cells, primary cells surgically obtained and established cell lines, and products derived from living cells. Products which can be derived from living cells include blood products such as insulin, the blood clotting factors (e.g. Factor V, VIII, VIII, IX, X, XI, XII), cytokines (e.g. interferon $\alpha$, $\beta$ or $\gamma$; the interleukins Il-1, Il-2, Il-3, etc.), complement proteins, antibodies, immune system regulators, recombinant proteins and other macromolecular products.

Treatment involves contact of the biological product with a solution comprising an adenosine derivative and, optionally, a deaminase inhibitor. Products may be sprayed, powdered, sprinkled, misted, subjected to pressurizing conditions, submerged, coated or otherwise administered compositions of the invention to foster contact between the composition and the organism. Contact may be encouraged by incubating compositions of the invention with the product. Incubations may be performed at between about 0° C. to about 70° C., preferably between about 18° C. and about 60° C., and more preferably at about 37° C. or about 56° C. For example, the biological product, which may be living, is placed in a sterile container and sprayed or immersed in a solution or sprinkled on as a powder containing an adenosine derivative and a deaminase inhibitor at an effective concentration. The deaminase inhibitor may not be necessary, for example, where there are no deaminases to inactivate. The product is maintained in this solution for a period of time necessary to effectively inactivate or destroy the infectious organism. This time period may be minutes to weeks, but is preferably between about one minute to one week, more preferably between about one hour to one day. The product is than removed from the solution, washed if necessary, and utilized as desired. As compositions of the invention are generally safe and non-toxic, separation of product from composition may not even be necessary, washing may not be necessary and the product may even be stored or shipped in the composition. In such cases, compositions of the invention may also contain additional components useful or desirable to accommodate the product during storage or shipping.

For example, biological products such as blood and blood products are required in vast quantities world-wide including areas of the world where fungal and fungal-like diseases are endemic. Food and food products (salts and spices, sugar, molasses, sorghum, alimentary paste, dairy products, oils) including grains and vegetables (corn, wheat, rice, barley, peas, soybean), breads, fruits (grapes, citrus fruits, bananas, apples, pears) and even fish and meats can be similarly treated. Maintaining an effective quantity of an adenosine derivative and, optionally, an effective quantity of a deaminase inhibitor in such supplies may prevent the spread of diseases from such products.

Other products which are required for medical uses include bone marrow and transplantable organs. Such products are typically obtained locally under emergency conditions. In such cases, there may be an undetected infection that would be passed to the patient receiving the product. Prophylactic treatment of these products would alleviate this risk and, as compositions of the invention are effective against a broad range of organisms, treatment only requires contact with this one composition. Multiple treatments would not be required or could be significantly reduced, increasing the overall chances of success for the therapy being administered to the patient.

Another embodiment of the invention comprises compositions for the treatment or prevention of a neoplastic disorder in a patient. The neoplastic disorder may be any disease or malady which could be characterized as a neoplasm, a tumor, a malignancy, a cancer or a disease which results in a relatively autonomous growth of cells. Composition contain an adenosine derivative such as a cordycepin or a cordycepin derivative, optionally, a deaminase inhibitor such as coformycin or deoxycoformycin, and a pharmaceutically acceptable carrier. The two agents may also be coupled together using techniques which are known to those skilled in the art.

Another embodiment of the invention is directed to methods for the treatment or prevention of a neoplastic disorder in a patient. Patients are preferably humans, but may be any mammal such as dogs, cats or rodents. Treatment involves means, such as discussed above, whereby the patient suspected or confirmed of having a neoplastic disorder is administered a composition of the invention. The composition may be administered by oral, parenteral, sublingual, rectal or enteral administration, or by pulmonary absorption or topical application. Parenteral administration may be by intravenous injection, subcutaneous injection, intramuscular injection, intra-arterial injection, intrathecal injection, intra peritoneal injection or direct injection or other administration to the site of the neoplasm. Injectable forms of administration are sometimes preferred for maximal effect. The neoplastic disorder may be a leukemia, lymphoma, sarcoma, carcinoma, neural cell tumor, squamous cell carcinoma, germ cell tumor, undifferentiated tumor, seminoma, melanoma, neuroblastoma, mixed cell tumor, metastatic neoplasia, neoplasia due to pathogenic infections or other malignancy. The adenosine derivative may be administered simultaneously with the deaminase inhibitor or prior to the deaminase inhibitor. Preferably the deaminase inhibitor is administered prior to the adenosine derivative.

In another embodiment of the invention, compositions of the invention may be used in any embodiment described herein in combination with other agents or therapies to maximize the effect of the compositions in an additive or synergistic manner. Patients are further administered another agent known to be effective against the neoplasia such as an alkylating agent, a purine or pyrimidine analog, a vinca or vinca-like alkaloid, an etoposide or etoposide-like drug, an antibiotic, a corticosteroid, a nitrosourea, an antimetabolite, a platinum based cytotoxic drug, a hormonal antagonist, an anti-androgen, an anti-estrogen, or a derivative, modification or combination of these agents. Therapies which are useful include augmention of conventional chemo-therapy, radiation therapy, antibody therapy, and other forms of therapy.

The following examples illustrate embodiments of the invention, but should not be viewed as limiting the scope of the invention.

EXAMPLES

Example 1 Inhibitory Concentrations of 3'-Deoxynucleosides in Cell Cultures

Cell cultures of various organisms were established in microtiter plates and maintained for a period of 24 hours after the addition of a 3'-deoxynucleoside (3'-dA, 3'-dG, 3'-dC, 3'-dU) (Calbiochem; San Diego, Calif.; Fluka Chemical; Ronkonkoma, N.Y.; Pharmacia Biotech; Piscataway, N.J.) or amphotericin B in µg/ml (Sigma Chemical; St. Louis, Mo.) as control. Results calculated as minimum inhibitory concentration (MIC) in micromoles per liter are shown in Table 1.

TABLE 1

| Organism | MIC µM | | | | Amphotericin B |
|---|---|---|---|---|---|
| | 3'-dA | 3'-dC | 3'-dG | 3'-dU | |
| C. albicans | 20 | >20 | >20 | >20 | <0.6 µg/ml |
| C. tropicalis | 20 | >20 | >20 | >20 | 1.25 µg/ml |
| Rhizopus | >20 | >20 | >20 | >20 | 2.50 µg/ml |
| C. neoformans | 20 | >20 | >20 | >20 | 2.50 µg/ml |
| A. fumigatus | 5 | 20 | >20 | >20 | 1.25 µg/ml |

From these results, deoxyadenosine (cordycepin) appears to demonstrate the most promise as an anti-fungal agent and inhibition observed is not non-specific nucleoside competition.

Example 2 Mortality in Candida albicans Infected Mice

Halen Sprague Dawley ICR mice were injected is with approximately $10^6$ cfu of Candida albicans. Twenty-four hours after injection, mice were treated for 10 days with the indicated agents: 3'-deoxyadenosine (Sigma Chemical; St. Louis, Mo.) at 1.5 mg/kg/day i.p., deoxycoformycin (Sigma Chemical; St. Louis, Mo.) at 0.4 mg/kg/day i.p., amphotericin B (Sigma Chemical; St. Louis, Mo.) at 1.0 mg/kg/day i.p. Survival after 25 days is shown in Tables 2 and 3.

TABLE 2

Survival of Mice Treated with Nucleosides

| Treatment | Survival After 25 Days |
|---|---|
| Control | 4/10 (40%) |
| 3'-deoxyadenosine | 3/10 (30%) |
| deoxycoformycin | 3/10 (30%) |
| 3'-deoxyadenosine + deoxycoformycin | 7/10 (70%) |
| amphotericin B | 9/10 (90%) |

TABLE 3

Survival of Mice Treated with Nucleosides

| Treatment | Survival After 15 Days |
|---|---|
| Control | 0/8 (00.0%) |
| 3'-Deoxyadenosine | 3/8 (37.5%) |
| Deoxycoformycin | 2/8 (25.0%) |
| 3'-Deoxyadenosine + Deoxycoformycin | 7/8 (87.5%) |
| Amphotericin B | 4/8 (50.0%) |

The combination of an adenine derivative plus a deaminase inhibitor increased survival over 30% as compared to controls after 25 days of observation in the first experiment and greater than amphotericin B after 15 days of observation in the second experiment.

Example 3 Time to Reach $LD_{50}$ of Various Agents in Mice

Halen Sprague Dawley ICR mice were injected with approximately $10^6$ cfu Candida albicans and treated for 10 days with the following agents: 3'-deoxyadenosine (Sigma Chemical; St. Louis, Mo.) at 1.5 mg/kg/day i.p., deoxycoformycin (Sigma Chemical; St. Louis, Mo.) at 0.4 mg/kg/day i.p., amphotericin B (Sigma Chemical; St. Louis, Mo.) at 1.0 mg/kg/day i.p. Time in days to reach $LD_{50}$ is shown in Table 4.

TABLE 4

$LD_{50}$ of Mice Treated with Nucleosides

| Treatment | Days to Reach $LD_{50}$ |
|---|---|
| Control | 6 |
| 3'-Deoxyadenosine | 9.5 |
| Deoxycoformycin | 5 |
| 3'-Deoxyadenosine + Deoxycoformycin | >30 |
| Amphotericin B | >30 |

The $LD_{50}$ of combination treatments was comparable with treatment with amphotericin B which is known to be safe and effective.

Example 4 Treatment of Neoplastic Cells in Tissue Culture

Cell lines were maintained in FCS/DMEM (GIBCO/BRL; Grand Island, N.Y.) at 37° C. with 5% $CO_2$ and treated with cordycepin, coformycin or cordycepin plus coformycin, or remain untreated as controls. In the presence of coformycin, cordycepin was specifically cytotoxic at $IC_{50}$ of less than 0.5 µM for the TdT-positive cells NALM-6, HPB-ALL, MOLT-4, CEM and 8402 cells. Cytotoxicity was seen in TdT-negative cells (HUT-102, K562, Raji, HL-60) only at concentrations 10–100 fold higher. The earliest manifestations of cytotoxic damage by cordycepin in TdT (terminal deoxynucleotidyl tranferase)-positive cells was the emergence of classic features of apoptosis such as membrane blebbing, volume loss, chromatin clumping and internucleosomal DNA digestion into 180 base pair (bp) multiples. In contrast, the cytotoxic damage seen when TdT-negative cells are exposed to high levels (greater than 5.0 µM) of cordycepin is associated with random DNA breakdown and necrosis. Since apoptosis in normal TdT-positive thymocytes is stimulated by protein kinase A (PK-A) activity, and inhibited by protein kinase C (PK-C) activity, PK-A and PK-C activities were measured in TdT-positive and TdT-negative cell lines after exposure to cordycepin.

PK-C activity was unchanged in both TdT-positive and TdT-negative cells. In contrast, PK-A activity increased 8–10 fold in TdT-positive cells within 2 hours of exposure to cordycepin, but unchanged in TdT-negative cells. Cordycepin plus coformycin had no effect in TdT-negative cells on either PK-A or PK-C activity. In cell free assays, endonucleolytic activity of recombinant TdT on supercoiled plasmid DNA was augmented by PK-A and especially in the presence of both calcium and magnesium. These data suggest that the cordycepin induced apoptotic cascade seen in TdT-positive cells may be mediated through PK-A activation and subsuquent phosphorylation of TdT. Phosphorylated TdT is able to thereby function as an endonuclease generating 180 bp DNA digests.

Example 5 Correlation of Cell Line Experiments in SCID Mouse Model

Figure 1:
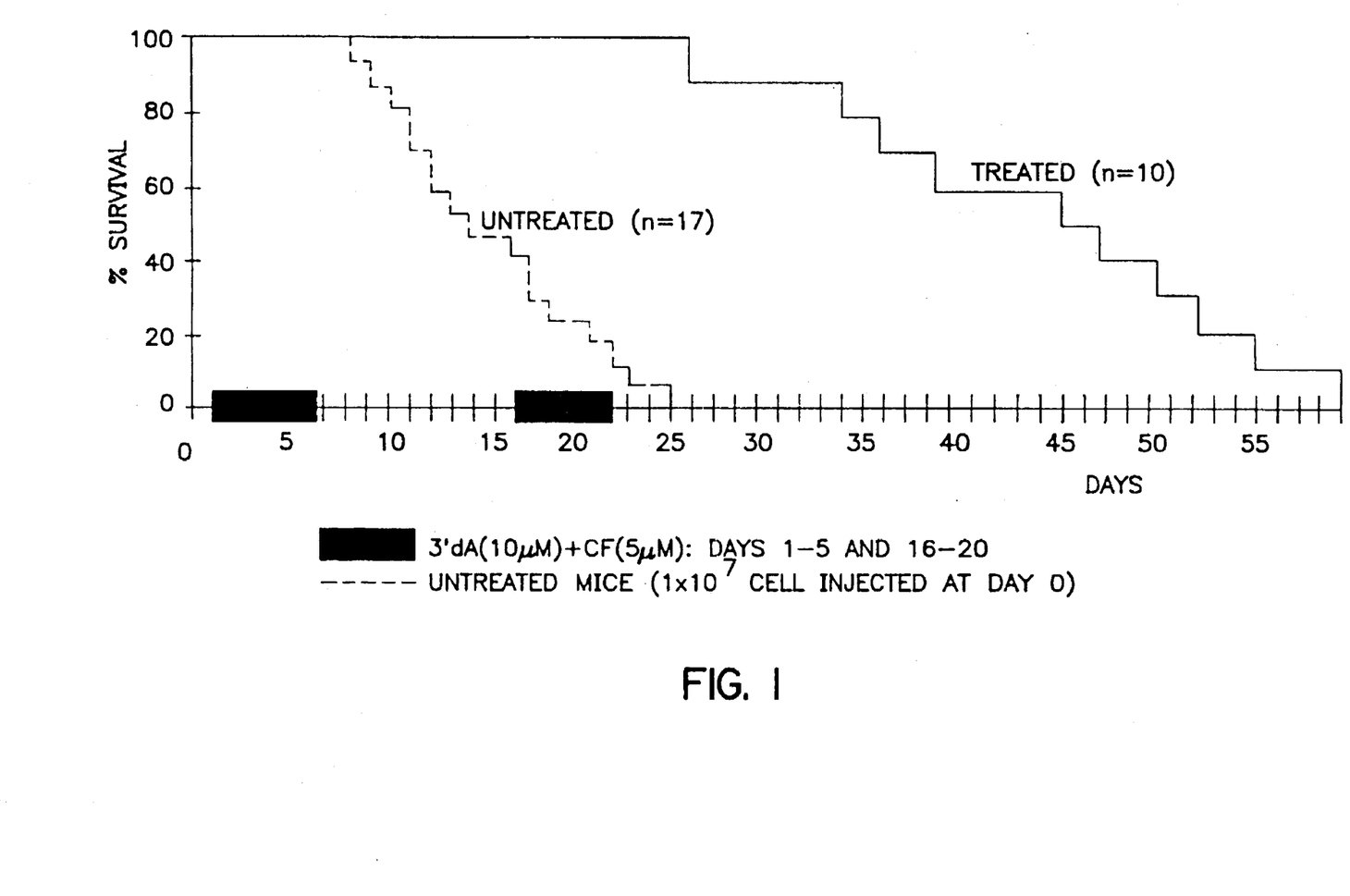
FIG. 1 Event free survival in the TdT-positive SCID mouse leukemia model using NALM-6 cells.

SCID (severe combined immunodeficient) mice were administered $10^7$ TdT-positive NALM-6 cells i.v. by tail vein at day 0. A filminant TdT-positive human leukemia/lymphoma xenograft was seen in 7 days. The $LD_{50}$ for this disease was 12 days and all untreated animals died by day 25. Ten mice were treated on day 1 with cordycepin (10 µM)/coformycin (5 µM) for two 5 day treatment periods (days 1–5 and 16–20) spaced two weeks apart. There was a significant prolongation of life in the treated group (median survival of 46 days versus 12 days in the untreated group). Results are shown in FIG. 1 and demonstrate an in vivo correlation of the studies performed in vitro.

Other embodiments and uses of the invention will be apparent to those skilled in the art from consideration of the specification and practice of the invention disclosed herein. It is intended that the specification and examples be considered exemplary only, with the true scope and spirit of the invention being indicated by the following claims.

We claim:

1. A method for the treatment of a patient infected with a fungal or fungal-like organism comprising administering to said patient a therapeutically effective amount of a purine nucleoside of the structure:

wherein $R_1$, $R_2$ and $R_3$ are each independently selected from the group consisting of hydrogen, hydroxyl, halides, alkyl and alkoxyl groups, amines and amides, sulfhydrals, nitryls, phosphoryls, and sulfinyl and sulfonyl groups.

2. The method of claim 1 wherein $R_1$ is —OH, —SH, —SCH$_3$ or —NHCH$_3$; $R_2$ is H, F, Cl, Br, I or NH$_2$; and $R_3$ is H, F, Cl, Br, I or CH$_3$.

3. The method of claim 1 further comprising the step of administering a therapeutically effective amount of a deaminase inhibitor to the patient.

4. The method of claim 3 wherein the deaminase inhibitor is administered prior to the purine nucleoside.

5. The method of claim 3 wherein said deaminase inhibitor is administered together with said purine nucleoside.

6. The method of claim 3 wherein the therapeutically effective amount of the deaminase inhibitor is between about 1 ng/kg patient weight to about 10 mg/kg patient weight.

7. The method of claim 3 wherein treatment results in a deaminase inhibitor concentration in at least one measurable fluid of the patient of between about 0.1 nM to about 10.0 µM.

8. The method of claim 3 wherein the purine nucleoside is administered in a two to twenty fold excess to the deaminase inhibitor.

9. The method of claim 3 wherein the purine nucleoside is administered in a five to ten fold excess to the deaminase inhibitor.

10. The method of claim 3 wherein the purine nucleoside is a cordycepin.

11. The method of claim 3 wherein the deaminase inhibitor is coformycin or deoxycoformycin.

12. The method of claim 3 wherein the patient has an organism load which is reduced at least 100-fold after treatment.

13. The method of claim 3 wherein the patient has a mycosis which is undetectable after treatment.

14. The method of claim 1 wherein the patient is a mammal.

15. The method of claim 1 wherein the mammal is selected from the group consisting of humans, dogs, cats, cattle, penguins, monkeys, horses, pigs, chickens and rodents.

16. The method of claim 1 wherein the fungal organism is a eukaryotic organism.

17. The method of claim 1 wherein the organism is selected from the group consisting of Candida krusei, C. glabrata, C. albicans and C. tropicalis, C. parapsilosis, Trichophyton rubrum, T. mentagrophytes, T. tonsurans, Microsporum audouini, M. canis and T. floccosum, Nocardia asteroides and N. brasiliensis, Actinomyces israelii, species of the genera Mucor, Absidia, Rhizopus, Cunninghamella and other Zygomycetes, Aspergillus fumigatus, A. flavus, A. niger and other species of Aspergillus, Crypttococcus neoformans, Paracoccidioides brasiliensis, Coccidioides immitis, Blastomycetes dermatitis and Histoplasma capsulatum.

18. The method of claim 1 wherein the fungal-like organism is a species of the genera Actinomyces or Nocardia.

19. The method of claim 4 wherein the purine nucleoside is administered parenterally, sublingually, enterally, by pulmonary absorption or by topical application.

20. The method of claim 19 wherein parenteral administration is by intravenous injection.

21. The method of claim 1 wherein the purine nucleoside is administered daily for multiple days.

22. The method of claim 1 wherein the therapeutically effective amount of the purine nucleoside is between about 1 ng/kg patient weight to about 10 mg/kg patient weight.

23. The method of claim 1 wherein treatment results in an purine nucleoside concentration in at least one measurable fluid of the patient of between about 0.1 nM to about 10.0 μM.

24. A method for the treatment of a biological product suspected of being contaminated with a fungal or fungal-like organism comprised of contacting said biological product with an effective amount of a purine nucleoside of the structure:

wherein $R_1$, $R_2$ and $R_3$ are each independently selected from the group consisting of hydrogen, hydroxyl, halides, alkyl and alkoxyl groups, amines and amides, sulfhydrals, nitryls, phosphoryls, and sulfinyl and sulfonyl groups.

25. The method of claim 24 wherein $R_1$ is —OH, —SH, —SCH$_3$ or —NHCH$_3$; $R_2$ is H, F, Cl, Br, I or NH$_2$; and $R_3$ is H, F, Cl, Br, I or CH$_3$.

26. The method of claim 24 wherein the purine nucleoside is cordycepin.

27. The method of claim 24 further comprising the step of administering an effective amount of a deaminase inhibitor.

28. The method of claim 27 wherein the deaminase inhibitor is coformycin or deoxycoformycin.

29. The method of claim 24 wherein the fungal organism is selected from the group consisting of *Candida krusei,. C. glabrata, C. parapsilosis, C. albicans* and *C. tropicalis, Trichophyton rubrum, T. mentagrophytes, T. tonsurans, Microsporum audouini, M. canis* and *T. floccosum, Nocardia asteroides* and *N. brasiliensis, Actinomyces israelii*, species of the genera Mucor, Absidia, Rhizolopus, Cunninghamella and other species of Mucorales, *Aspergillus fumigatus, A. flavus, A. niger* and other species of Aspergillus, *Cryptococcus neoformans, Paracoccidioides brasiliensis, Blastomycetes dermatitis, Coccidioides immitis* and *Histoplasma capsulatum*.

30. The method of claim 24 wherein the fungal-like organism is selected from the group consisting of *Actinomyces israelii, Nocardia asteroides* and *N. brasiliensis*.

31. The method of claim 24 wherein the biological product comprises living cells.

32. The method of claim 31 wherein the living cells are selected from the group consisting of whole blood, fractionated blood, plasma, sentra, bone marrow and transplantable organs.

33. The method of claim 24 wherein the biological product is a food product.

34. The method of claim 33 wherein the food product is selected from the group consisting of rice, wheat, barley, corn, soybeans, breads, oils, sugars, spices, dairy products, alimentary paste, vegetables and fruit.

35. The method of claims 24 wherein the biological product is derived from living cells.

36. The method of claim 35 wherein the biological product derived from living cells is selected from the group consisting of cytokines, antibodies, immune system regulators, recombinant proteins and blood products.

37. The method of claim 24 wherein the biological product is incubated in a solution comprising said purine nucleoside.

38. The method of claim 37 wherein said solution further comprises a deaminase inhibitor.

39. The method of claim 24 wherein the biological product is powdered with a powder comprising said purine nucleoside.

40. The method of claim 39 wherein said powder further comprises a deaminase inhibitor.

41. A method for the treatment of a biological product to prevent said product from being contaminated with a fungal or fungal-like organism comprised of contacting said product with an effective amount of a purine nucleoside of the structure:

wherein $R_1$, $R_2$ and $R_3$ are each independently selected from the group consisting of hydrogen, hydroxyl, halides, alkyl and alkoxyl groups, amines and amides, sulfhydrals, nitryls, phosphoryls, and sulfinyl and sulfonyl groups.

42. The method of claim 41 wherein $R_1$ is —OH, —SH, —SCH, or —NHCH$_3$; $R_2$ is H, F, Cl, Br, I or NH$_2$; and $R_3$ is H, F, Cl, Br, I or CH$_3$.

43. The method of claim 41 wherein the purine nucleoside is cordycepin.

44. The method of claim 41 further comprising the step of administering an effective amount of a deaminase inhibitor.

45. The method of claim 44 wherein the deaminase inhibitor is coformycin or deoxycoformycin.

46. The method of claim 41 wherein the biological product is incubated in a solution comprising said purine nucleoside.

47. The method of claim 46 wherein said solution further comprises a deaminase inhibitor.

48. The method of claim 41 wherein the fungal organism is selected from the group consisting of *Candida krusei, C. glabrata, C. parapsilosis, C. albicans* and *C. tropicalis, Trichophyton rubrum , T. mentagrophytes, T. tonsurans, Microsporum audouini, M. canis* and *T. floccosum, Nocardia asteroides* and *N. brasiliensis, Actinomyces israelii*, species of the genera Mucor, Absidia, Rhizopus, Cunninghamella and other species of Mucorales, *Aspergillus fumigatus, A. flavus, A. niger* and other species of Aspergillus, *Crypto-

*coccus neoformans, Paracoccidioides brasiliensis, Blastomycetes dermatitis, Coccidioides immitis* and *Histoplasma capsulatum*.

49. The method of claim 41 wherein the fungal-like organism is selected from the group consisting of *Actinomyces israelii, Nocardia asteroides* and *N. brasiliensis*.

50. The method of claim 41 wherein the biological product comprises living cells.

51. The method of claim 41 wherein the living cells are selected from the group consisting of whole blood, fractionated blood, plasma, serum, bone marrow and transplantable organs.

52. The method of claim 41 wherein the biological product is a food product.

53. The method of claim 52 wherein the food product is selected from the group consisting of rice, wheat, barley, corn, soybeans, breads, oils, sugars, spices, dairy products, alimentary paste, vegetables and fruit.

54. The method of claims 41 wherein the biological product is derived from living cells.

55. The method of claim 54 wherein the biological product derived from living cells is selected from the group consisting of cytokines, antibodies, immune system regulators, recombinant proteins and blood products.

56. The method of claim 41 wherein the biological product is powdered with a powder comprising said purine nucleoside.

57. The method of claim 56 wherein said powder further comprises a deaminase inhibitor.

* * * * *